(12) United States Patent
Reggiardo

(10) Patent No.: US 8,512,246 B2
(45) Date of Patent: Aug. 20, 2013

(54) METHOD AND APPARATUS FOR PROVIDING PEAK DETECTION CIRCUITRY FOR DATA COMMUNICATION SYSTEMS

(75) Inventor: Christopher V. Reggiardo, Castro Valley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 551 days.

(21) Appl. No.: 12/724,383

(22) Filed: Mar. 15, 2010

(65) Prior Publication Data
US 2010/0171610 A1 Jul. 8, 2010

Related U.S. Application Data

(63) Continuation of application No. 10/832,512, filed on Apr. 27, 2004, now Pat. No. 7,679,407.

(60) Provisional application No. 60/466,243, filed on Apr. 28, 2003.

(51) Int. Cl.
*A61B 5/00* (2006.01)
(52) U.S. Cl.
USPC .................. 600/365; 340/539.1; 702/25
(58) Field of Classification Search
None
See application file for complete search history.

(56) References Cited

U.S. PATENT DOCUMENTS

| | | | |
|---|---|---|---|
| 2,508,253 A | 5/1950 | Haggardt | |
| 2,915,579 A | 12/1959 | Mendelsohn | |
| 3,374,337 A | 3/1968 | Burley | |
| 3,510,747 A | 5/1970 | Petrides | |
| 3,541,892 A | 11/1970 | Kubinek et al. | |
| 3,606,592 A | 9/1971 | Madurski et al. | |
| 3,750,687 A | 8/1973 | Williams | |
| 3,843,455 A | 10/1974 | Bier | |
| 3,923,060 A | 12/1975 | Ellinwood | |
| 3,930,493 A | 1/1976 | Williamson | |
| 3,938,140 A | 2/1976 | Garcia et al. | |
| 3,994,799 A | 11/1976 | Yao et al. | |
| 4,018,547 A | 4/1977 | Rogen | |

(Continued)

FOREIGN PATENT DOCUMENTS

| CA | 2143172 | 7/2005 |
|---|---|---|
| CA | 2396613 | 3/2008 |

(Continued)

OTHER PUBLICATIONS

"An Electrochemical Slow Flow Meter", http://gore.ocean.washington.edu/research/slow_flow_meter.html, 2005, 3 pages.

(Continued)

*Primary Examiner* — Michael Kahelin
*Assistant Examiner* — Mitchell Alter
(74) *Attorney, Agent, or Firm* — Jackson & Co., LLP

(57) ABSTRACT

Method and apparatus for providing a peak detection circuit comprising a diode including an input terminal and an output terminal the input terminal of the diode configured to receive an input signal, a capacitor operatively coupled to the output terminal of the diode, an output terminal operatively coupled to the capacitor and the output terminal of the diode for outputting an output signal is provided. Other equivalent switching configuration is further provided to effectively detect and compensate for a voltage droop from a power supply signal, as well as to electrically isolate the voltage droop from the system circuitry.

20 Claims, 6 Drawing Sheets

(56) References Cited

U.S. PATENT DOCUMENTS

| | | |
|---|---|---|
| 4,048,551 A | 9/1977 | Bosik |
| 4,121,282 A | 10/1978 | Ohsawa |
| 4,146,029 A | 3/1979 | Ellinwood |
| 4,172,770 A | 10/1979 | Semersky et al. |
| 4,193,397 A | 3/1980 | Tucker et al. |
| 4,268,173 A | 5/1981 | Barnard et al. |
| 4,288,793 A | 9/1981 | Lotscher |
| 4,309,156 A | 1/1982 | Gonner et al. |
| 4,360,019 A | 11/1982 | Potner et al. |
| 4,362,052 A | 12/1982 | Heath et al. |
| 4,401,122 A | 8/1983 | Clark, Jr. |
| 4,439,197 A | 3/1984 | Honda et al. |
| 4,441,968 A | 4/1984 | Emmer et al. |
| 4,447,224 A | 5/1984 | DeCant, Jr. et al. |
| 4,458,686 A | 7/1984 | Clark, Jr. |
| 4,467,811 A | 8/1984 | Clark, Jr. |
| 4,472,113 A | 9/1984 | Rogen |
| 4,474,309 A | 10/1984 | Solomon |
| 4,486,190 A | 12/1984 | Reinicke |
| 4,494,950 A | 1/1985 | Fischell |
| 4,512,348 A | 4/1985 | Uchigaki et al. |
| 4,524,343 A | 6/1985 | Morgan et al. |
| 4,529,401 A | 7/1985 | Leslie et al. |
| 4,531,235 A * | 7/1985 | Brusen ................. 455/273 |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,574,809 A | 3/1986 | Talish et al. |
| 4,633,878 A | 1/1987 | Bombardieri |
| 4,655,880 A | 4/1987 | Liu |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A | 3/1989 | Palmer |
| 4,850,959 A | 7/1989 | Findl |
| 4,851,827 A | 7/1989 | Nicholas |
| 4,866,396 A | 9/1989 | Tamura |
| 4,883,409 A | 11/1989 | Strohmeier et al. |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,880 A | 9/1991 | Harm et al. |
| 5,061,914 A | 10/1991 | Bush et al. |
| 5,078,683 A | 1/1992 | Sancoff et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,155,695 A | 10/1992 | Stein |
| 5,190,041 A | 3/1993 | Palti |
| 5,205,819 A | 4/1993 | Ross et al. |
| 5,207,666 A | 5/1993 | Idriss et al. |
| 5,211,371 A | 5/1993 | Coffee |
| 5,211,626 A | 5/1993 | Frank et al. |
| 5,223,822 A | 6/1993 | Stommes et al. |
| 5,262,305 A | 11/1993 | Heller et al. |
| 5,264,104 A | 11/1993 | Gregg et al. |
| 5,267,026 A | 11/1993 | Kawahara et al. |
| 5,278,997 A | 1/1994 | Martin |
| 5,284,423 A | 2/1994 | Holdsworth et al. |
| 5,284,425 A | 2/1994 | Holtermann et al. |
| 5,291,614 A | 3/1994 | Baker et al. |
| 5,291,887 A | 3/1994 | Stanley et al. |
| 5,320,725 A | 6/1994 | Gregg et al. |
| 5,324,599 A | 6/1994 | Oyama et al. |
| 5,325,280 A | 6/1994 | Tortola et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,382,331 A | 1/1995 | Banks |
| 5,390,671 A | 2/1995 | Lord et al. |
| 5,391,250 A | 2/1995 | Cheney, II et al. |
| 5,398,681 A | 3/1995 | Kupershmidt |
| 5,404,585 A | 4/1995 | Vimpari et al. |
| 5,406,301 A | 4/1995 | Ravid |
| 5,445,611 A | 8/1995 | Eppstein et al. |
| 5,448,992 A | 9/1995 | Kupershmidt |
| 5,458,140 A | 10/1995 | Eppstein et al. |
| 5,469,025 A | 11/1995 | Kanemori et al. |
| 5,479,486 A | 12/1995 | Saji |
| 5,494,562 A | 2/1996 | Maley et al. |
| 5,497,772 A | 3/1996 | Schulman et al. |
| 5,505,713 A | 4/1996 | Van Antwerp |
| 5,507,288 A | 4/1996 | Bocker et al. |
| 5,515,390 A | 5/1996 | Benton |
| 5,517,434 A | 5/1996 | Hanson et al. |
| 5,526,844 A | 6/1996 | Kamen et al. |
| 5,527,288 A | 6/1996 | Gross et al. |
| 5,532,686 A | 7/1996 | Urbas et al. |
| 5,533,389 A | 7/1996 | Kamen et al. |
| 5,543,678 A | 8/1996 | Hoiberg |
| 5,559,528 A | 9/1996 | Ravid |
| 5,568,400 A | 10/1996 | Stark et al. |
| 5,568,806 A | 10/1996 | Cheney, II et al. |
| 5,573,506 A | 11/1996 | Vasko |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,596,261 A | 1/1997 | Suyama |
| 5,601,435 A | 2/1997 | Quy |
| 5,604,404 A | 2/1997 | Sahara |
| 5,615,671 A | 4/1997 | Schoonen et al. |
| 5,620,579 A | 4/1997 | Genshaw et al. |
| 5,622,413 A | 4/1997 | Kim et al. |
| 5,622,482 A | 4/1997 | Lee |
| 5,628,324 A | 5/1997 | Sarbach |
| 5,634,468 A | 6/1997 | Platt et al. |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,665,222 A | 9/1997 | Heller et al. |
| 5,671,301 A | 9/1997 | Kupershmidt |
| 5,685,844 A | 11/1997 | Marttila |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,724,030 A | 3/1998 | Urbas et al. |
| 5,738,220 A | 4/1998 | Geszler |
| 5,741,211 A | 4/1998 | Renirie et al. |
| 5,748,872 A | 5/1998 | Norman |
| 5,749,907 A | 5/1998 | Mann |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,804,047 A | 9/1998 | Karube et al. |
| 5,812,102 A | 9/1998 | Sprole et al. |
| 5,814,020 A | 9/1998 | Gross |
| 5,814,599 A | 9/1998 | Mitragotri et al. |
| 5,815,303 A | 9/1998 | Berlin |

| | | | | | | |
|---|---|---|---|---|---|---|
| 5,822,715 | A | 10/1998 | Worthington et al. | 6,155,992 A | 12/2000 | Henning et al. |
| 5,825,488 | A | 10/1998 | Kohl et al. | 6,157,442 A | 12/2000 | Raskas |
| 5,833,603 | A | 11/1998 | Kovacs et al. | 6,160,449 A | 12/2000 | Klomsdorf et al. |
| 5,848,990 | A | 12/1998 | Cirelli et al. | 6,162,202 A | 12/2000 | Sicurelli et al. |
| 5,851,197 | A | 12/1998 | Marano et al. | 6,162,611 A | 12/2000 | Heller et al. |
| 5,856,631 | A | 1/1999 | Julien | 6,164,284 A | 12/2000 | Schulman et al. |
| 5,858,001 | A | 1/1999 | Tsals et al. | 6,173,160 B1 | 1/2001 | Liimatainen |
| 5,873,026 | A | 2/1999 | Reames | 6,175,752 B1 | 1/2001 | Say et al. |
| 5,875,417 | A | 2/1999 | Golden | 6,180,416 B1 | 1/2001 | Kurnik et al. |
| 5,885,211 | A | 3/1999 | Eppstein et al. | 6,185,452 B1 | 2/2001 | Schulman et al. |
| 5,891,049 | A | 4/1999 | Cyrus et al. | 6,186,982 B1 | 2/2001 | Gross et al. |
| 5,899,855 | A | 5/1999 | Brown | 6,192,891 B1 | 2/2001 | Gravel et al. |
| 5,913,833 | A | 6/1999 | Elstrom et al. | 6,200,265 B1 | 3/2001 | Walsh et al. |
| 5,918,603 | A | 7/1999 | Brown | 6,201,980 B1 | 3/2001 | Darrow et al. |
| 5,919,167 | A | 7/1999 | Mulhauser | 6,203,288 B1 | 3/2001 | Kottke |
| 5,923,512 | A | 7/1999 | Brownlow et al. | 6,206,841 B1 | 3/2001 | Cunningham et al. |
| 5,931,814 | A | 8/1999 | Alex et al. | 6,208,894 B1 | 3/2001 | Schulman et al. |
| 5,947,921 | A | 9/1999 | Johnson et al. | 6,212,416 B1 | 4/2001 | Ward et al. |
| 5,948,512 | A | 9/1999 | Kubota et al. | 6,215,206 B1 | 4/2001 | Chitayat |
| 5,951,485 | A | 9/1999 | Cyrus et al. | 6,222,514 B1 | 4/2001 | DeLuca |
| 5,951,582 | A | 9/1999 | Thorne et al. | 6,228,100 B1 | 5/2001 | Schraga |
| 5,951,836 | A | 9/1999 | McAleer et al. | 6,232,370 B1 | 5/2001 | Kubota et al. |
| 5,954,643 | A | 9/1999 | VanAntwerp et al. | 6,233,471 B1 | 5/2001 | Berner et al. |
| 5,965,380 | A | 10/1999 | Heller et al. | 6,233,539 B1 | 5/2001 | Brown |
| 5,968,011 | A | 10/1999 | Larsen et al. | 6,242,961 B1 | 6/2001 | Liu et al. |
| 5,971,922 | A | 10/1999 | Arita et al. | 6,245,060 B1 | 6/2001 | Loomis et al. |
| 5,972,199 | A | 10/1999 | Heller et al. | 6,248,067 B1 | 6/2001 | Causey, III et al. |
| 5,993,411 | A | 11/1999 | Choi | 6,262,708 B1 | 7/2001 | Chu |
| 5,994,878 | A | 11/1999 | Ostergaard et al. | 6,272,364 B1 | 8/2001 | Kurnik |
| 5,997,501 | A | 12/1999 | Gross et al. | 6,278,425 B1 | 8/2001 | DeLuca |
| 6,001,067 | A | 12/1999 | Shults et al. | 6,280,587 B1 | 8/2001 | Matsumoto |
| 6,002,961 | A | 12/1999 | Mitragotri et al. | 6,283,926 B1 | 9/2001 | Cunningham et al. |
| 6,011,486 | A | 1/2000 | Casey | 6,283,951 B1 | 9/2001 | Flaherty et al. |
| 6,014,577 | A | 1/2000 | Henning et al. | 6,284,478 B1 | 9/2001 | Heller et al. |
| 6,017,328 | A | 1/2000 | Fischell et al. | 6,288,653 B1 | 9/2001 | Shih |
| 6,018,678 | A | 1/2000 | Mitragotri et al. | 6,291,200 B1 | 9/2001 | LeJeune et al. |
| 6,023,629 | A | 2/2000 | Tamada | 6,293,925 B1 | 9/2001 | Safabash et al. |
| 6,024,539 | A | 2/2000 | Blomquist | 6,294,997 B1 | 9/2001 | Paratore et al. |
| 6,026,320 | A | 2/2000 | Carlson et al. | 6,295,506 B1 | 9/2001 | Heinonen et al. |
| 6,027,459 | A | 2/2000 | Shain et al. | 6,298,254 B2 | 10/2001 | Tamada |
| 6,027,496 | A | 2/2000 | Loomis et al. | 6,298,255 B1 | 10/2001 | Cordero et al. |
| 6,027,692 | A | 2/2000 | Galen et al. | 6,299,578 B1 | 10/2001 | Kurnik et al. |
| 6,032,059 | A | 2/2000 | Henning et al. | 6,301,499 B1 | 10/2001 | Carlson et al. |
| 6,041,253 | A | 3/2000 | Kost et al. | 6,306,104 B1 | 10/2001 | Cunningham et al. |
| 6,041,665 | A | 3/2000 | Hussain | 6,309,351 B1 | 10/2001 | Kurnik et al. |
| 6,059,546 | A | 5/2000 | Brenan et al. | 6,312,888 B1 | 11/2001 | Wong et al. |
| 6,063,039 | A | 5/2000 | Cunningham et al. | 6,315,721 B2 | 11/2001 | Schulman et al. |
| 6,064,368 | A | 5/2000 | Kang | 6,326,160 B1 | 12/2001 | Dunn et al. |
| 6,066,243 | A | 5/2000 | Anderson et al. | 6,329,161 B1 | 12/2001 | Heller et al. |
| 6,067,017 | A | 5/2000 | Stewart et al. | 6,331,244 B1 | 12/2001 | Lewis et al. |
| 6,067,463 | A | 5/2000 | Jeng et al. | 6,338,790 B1 | 1/2002 | Feldman et al. |
| 6,071,249 | A | 6/2000 | Cunningham et al. | 6,341,232 B1 | 1/2002 | Conn et al. |
| 6,071,251 | A | 6/2000 | Cunningham et al. | 6,356,776 B1 | 3/2002 | Berner et al. |
| 6,073,031 | A | 6/2000 | Helstab et al. | 6,360,888 B1 | 3/2002 | McIvor et al. |
| 6,077,660 | A | 6/2000 | Wong et al. | 6,366,793 B1 | 4/2002 | Bell et al. |
| 6,081,104 | A * | 6/2000 | Kern ............................ 323/268 | 6,368,141 B1 | 4/2002 | VanAntwerp et al. |
| 6,082,289 | A | 7/2000 | Cavallaro | 6,368,274 B1 | 4/2002 | Van Antwerp et al. |
| 6,083,710 | A | 7/2000 | Heller et al. | 6,372,371 B1 | 4/2002 | Iarochenko et al. |
| 6,085,871 | A | 7/2000 | Karamata | 6,375,344 B1 | 4/2002 | Hanson et al. |
| 6,086,575 | A | 7/2000 | Mejslov | 6,375,638 B2 | 4/2002 | Nason et al. |
| 6,091,975 | A | 7/2000 | Daddona et al. | 6,377,894 B1 | 4/2002 | Deweese et al. |
| 6,091,987 | A | 7/2000 | Thompson | 6,379,301 B1 | 4/2002 | Worthington et al. |
| 6,093,156 | A | 7/2000 | Cunningham et al. | 6,381,496 B1 | 4/2002 | Meadows et al. |
| 6,093,172 | A | 7/2000 | Funderburk et al. | 6,387,048 B1 | 5/2002 | Schulman et al. |
| 6,103,033 | A | 8/2000 | Say et al. | 6,393,318 B1 | 5/2002 | Conn et al. |
| 6,120,676 | A | 9/2000 | Heller et al. | 6,400,974 B1 | 6/2002 | Lesho |
| 6,121,009 | A | 9/2000 | Heller et al. | 6,403,944 B1 | 6/2002 | MacKenzie et al. |
| 6,129,823 | A | 10/2000 | Hughes et al. | 6,405,066 B1 | 6/2002 | Essenpreis et al. |
| 6,130,623 | A | 10/2000 | MacLellan et al. | 6,408,402 B1 | 6/2002 | Norman |
| 6,132,371 | A | 10/2000 | Dempsey et al. | 6,413,393 B1 | 7/2002 | Van Antwerp et al. |
| 6,134,461 | A | 10/2000 | Say et al. | 6,416,471 B1 | 7/2002 | Kumar et al. |
| 6,142,939 | A | 11/2000 | Eppstein et al. | 6,417,074 B2 | 7/2002 | Kopley et al. |
| 6,143,164 | A | 11/2000 | Heller et al. | 6,418,332 B1 | 7/2002 | Mastrototaro et al. |
| 6,144,303 | A | 11/2000 | Federman | 6,418,346 B1 | 7/2002 | Nelson et al. |
| 6,144,869 | A | 11/2000 | Berner et al. | 6,419,642 B1 | 7/2002 | Marchitto et al. |
| 6,144,871 | A | 11/2000 | Saito et al. | 6,425,829 B1 | 7/2002 | Julien |
| 6,144,922 | A | 11/2000 | Douglas et al. | 6,427,088 B1 | 7/2002 | Bowman, IV et al. |
| 6,147,342 | A | 11/2000 | Kucher | 6,432,585 B1 | 8/2002 | Kawakami et al. |
| 6,154,855 | A | 11/2000 | Norman | 6,437,379 B2 | 8/2002 | Kopley et al. |

| | | |
|---|---|---|
| 6,438,385 B1 | 8/2002 | Heinonen et al. |
| 6,438,414 B1 | 8/2002 | Conn et al. |
| 6,442,413 B1 | 8/2002 | Silver |
| 6,445,374 B2 | 9/2002 | Albert et al. |
| 6,461,329 B1 | 10/2002 | Van Antwerp et al. |
| 6,462,162 B2 | 10/2002 | Van Antwerp et al. |
| 6,464,848 B1 | 10/2002 | Matsumoto |
| 6,466,807 B1 | 10/2002 | Dobson et al. |
| 6,466,810 B1 | 10/2002 | Ward et al. |
| 6,468,222 B1 | 10/2002 | Mault et al. |
| 6,471,980 B2 | 10/2002 | Sirhan et al. |
| 6,472,991 B1 | 10/2002 | Schulman et al. |
| 6,475,196 B1 | 11/2002 | Vachon |
| 6,478,736 B1 | 11/2002 | Mault |
| 6,480,730 B2 | 11/2002 | Darrow et al. |
| 6,482,158 B2 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,485,138 B1 | 11/2002 | Kubota et al. |
| 6,485,461 B1 | 11/2002 | Mason et al. |
| 6,485,465 B2 | 11/2002 | Morberg et al. |
| 6,492,180 B2 | 12/2002 | Brown et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,506,168 B1 | 1/2003 | Fathallah et al. |
| 6,513,532 B2 | 2/2003 | Mault et al. |
| 6,514,460 B1 | 2/2003 | Fendrock |
| 6,514,689 B2 | 2/2003 | Han et al. |
| 6,514,718 B2 | 2/2003 | Heller et al. |
| 6,520,326 B2 | 2/2003 | McIvor et al. |
| 6,522,530 B2 | 2/2003 | Bang |
| 6,525,330 B2 | 2/2003 | Paolini et al. |
| 6,526,298 B1 | 2/2003 | Khalil et al. |
| 6,529,772 B2 | 3/2003 | Carlson et al. |
| 6,530,915 B1 | 3/2003 | Eppstein et al. |
| 6,535,753 B1 | 3/2003 | Raskas |
| 6,537,243 B1 | 3/2003 | Henning et al. |
| 6,540,675 B2 | 4/2003 | Aceti et al. |
| 6,540,891 B1 | 4/2003 | Stewart et al. |
| 6,543,224 B1 | 4/2003 | Barooah |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 * | 5/2003 | Heller et al. ............... 600/347 |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |
| 6,565,738 B1 | 5/2003 | Henning et al. |
| 6,569,157 B1 | 5/2003 | Shain et al. |
| 6,571,128 B2 | 5/2003 | Lebel et al. |
| 6,571,200 B1 | 5/2003 | Mault |
| 6,574,510 B2 | 6/2003 | Von Arx et al. |
| 6,576,117 B1 | 6/2003 | Iketaki et al. |
| 6,577,899 B2 | 6/2003 | Lebel et al. |
| 6,579,231 B1 | 6/2003 | Phipps |
| 6,579,498 B1 | 6/2003 | Eglise |
| 6,579,690 B1 | 6/2003 | Bonnecaze et al. |
| 6,582,393 B2 | 6/2003 | Sage, Jr. |
| 6,585,644 B2 | 7/2003 | Lebel et al. |
| 6,586,971 B1 | 7/2003 | Naffziger et al. |
| 6,587,705 B1 | 7/2003 | Kim et al. |
| 6,589,229 B1 | 7/2003 | Connelly et al. |
| 6,594,514 B2 | 7/2003 | Berner et al. |
| 6,595,919 B2 | 7/2003 | Berner et al. |
| 6,596,016 B1 | 7/2003 | Vreman et al. |
| 6,600,997 B2 | 7/2003 | Deweese et al. |
| 6,602,469 B1 | 8/2003 | Maus et al. |
| 6,607,509 B2 | 8/2003 | Bobroff et al. |
| 6,610,012 B2 | 8/2003 | Mault |
| 6,612,306 B1 | 9/2003 | Mault |
| 6,615,061 B1 | 9/2003 | Khalil et al. |
| 6,615,074 B2 | 9/2003 | Mickle et al. |
| 6,618,603 B2 | 9/2003 | Varalli et al. |
| 6,620,106 B2 | 9/2003 | Mault |
| 6,623,501 B2 | 9/2003 | Heller et al. |
| 6,629,934 B2 | 10/2003 | Mault et al. |
| 6,633,095 B1 | 10/2003 | Swope et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,656,158 B2 | 12/2003 | Gregory et al. |
| 6,656,159 B2 | 12/2003 | Flaherty |
| 6,659,948 B2 | 12/2003 | Lebel et al. |
| 6,659,980 B2 | 12/2003 | Morberg et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,670,806 B2 | 12/2003 | Wendt et al. |
| 6,679,841 B2 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Starkweather et al. |
| 6,695,885 B2 | 2/2004 | Schulman et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,736,777 B2 | 5/2004 | Kim et al. |
| 6,736,797 B1 | 5/2004 | Larsen et al. |
| 6,738,654 B2 | 5/2004 | Sohrab |
| 6,740,059 B2 | 5/2004 | Flaherty |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,749,587 B2 | 6/2004 | Flaherty |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,773,563 B2 | 8/2004 | Matsumoto |
| 6,779,984 B2 | 8/2004 | Lilie et al. |
| 6,789,195 B1 | 9/2004 | Prihoda et al. |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,830,558 B2 | 12/2004 | Flaherty et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |

| Patent | Date | Inventor |
|---|---|---|
| 6,872,200 B2 | 3/2005 | Mann et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,764 B2 | 8/2005 | Aceti et al. |
| 6,927,749 B1 | 8/2005 | Klemm |
| 6,931,327 B2 | 8/2005 | Goode, Jr. et al. |
| 6,936,029 B2 | 8/2005 | Mann et al. |
| 6,940,403 B2 | 9/2005 | Kail, IV |
| 6,941,163 B2 | 9/2005 | Ford et al. |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,960,192 B1 | 11/2005 | Flaherty et al. |
| 6,961,448 B2 | 11/2005 | Nichols et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |
| 7,005,857 B2 | 2/2006 | Stiene et al. |
| 7,006,858 B2 | 2/2006 | Silver et al. |
| 7,009,511 B2 | 3/2006 | Mazar et al. |
| 7,010,356 B2 | 3/2006 | Jog et al. |
| 7,011,630 B2 | 3/2006 | Desai et al. |
| 7,018,360 B2 | 3/2006 | Flaherty et al. |
| 7,020,508 B2 | 3/2006 | Stivoric et al. |
| 7,024,236 B2 | 4/2006 | Ford et al. |
| 7,024,245 B2 | 4/2006 | Lebel et al. |
| 7,024,249 B2 | 4/2006 | Weisner et al. |
| 7,025,743 B2 | 4/2006 | Mann et al. |
| 7,029,444 B2 | 4/2006 | Shin et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,052,251 B2 | 5/2006 | Nason et al. |
| 7,058,437 B2 | 6/2006 | Buse et al. |
| 7,058,453 B2 | 6/2006 | Nelson et al. |
| 7,060,031 B2 | 6/2006 | Webb et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,082,334 B2 | 7/2006 | Boute et al. |
| 7,083,593 B2 | 8/2006 | Stultz |
| 7,086,277 B2 | 8/2006 | Tess et al. |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,711 B2 | 9/2006 | Vogel et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,125,382 B2 | 10/2006 | Zhou et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,137,964 B2 | 11/2006 | Flaherty |
| 7,144,384 B2 | 12/2006 | Gorman et al. |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |
| 7,167,818 B2 | 1/2007 | Brown |
| 7,171,274 B2 | 1/2007 | Starkweather et al. |
| 7,174,199 B2 | 2/2007 | Berner et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,193,521 B2 | 3/2007 | Morberg et al. |
| 7,198,603 B2 | 4/2007 | Penner et al. |
| 7,202,734 B1 | 4/2007 | Raab |
| 7,203,549 B2 | 4/2007 | Schommer et al. |
| 7,205,409 B2 | 4/2007 | Pei et al. |
| 7,208,119 B1 | 4/2007 | Kurtock et al. |
| 7,211,048 B1 | 5/2007 | Najafi et |
| 7,218,017 B1 | 5/2007 | Chitayet et al. |
| 7,225,535 B2 | 6/2007 | Feldman et al. |
| 7,226,278 B2 | 6/2007 | Nason et al. |
| 7,226,442 B2 | 6/2007 | Sheppard, Jr. et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,666 B2 | 8/2007 | Brown |
| 7,266,400 B2 | 9/2007 | Fine et al. |
| 7,267,665 B2 | 9/2007 | Steil et al. |
| 7,276,029 B2 | 10/2007 | Goode, Jr. et al. |
| 7,283,867 B2 | 10/2007 | Strother et al. |
| 7,291,497 B2 | 11/2007 | Holmes et al. |
| 7,295,867 B2 | 11/2007 | Berner et al. |
| 7,299,080 B2 | 11/2007 | Acosta et al. |
| 7,303,549 B2 | 12/2007 | Flaherty et al. |
| 7,310,544 B2 | 12/2007 | Brister et al. |
| 7,323,091 B1 | 1/2008 | Gillette et al. |
| 7,324,850 B2 | 1/2008 | Persen et al. |
| 7,324,949 B2 | 1/2008 | Bristol et al. |
| 7,343,188 B2 | 3/2008 | Sohrab |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,371,247 B2 | 5/2008 | Boeker et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,419,573 B2 | 9/2008 | Gundel |
| 7,424,318 B2 | 9/2008 | Brister et al. |
| 7,436,511 B2 | 10/2008 | Ruchti et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,138 B2 | 1/2009 | Kogan et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,565,197 B2 | 7/2009 | Haubrich et al. |
| 7,574,266 B2 | 8/2009 | Dudding et al. |
| 7,583,190 B2 | 9/2009 | Reggiardo et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,620,437 B2 | 11/2009 | Reggiardo |
| 7,632,228 B2 | 12/2009 | Brauker et al. |

| Patent | Date | Name |
|---|---|---|
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,741,734 B2 | 6/2010 | Joannopoulos et al. |
| 7,771,352 B2 | 8/2010 | Shults et al. |
| 7,774,145 B2 | 8/2010 | Brauker et al. |
| 7,775,444 B2 | 8/2010 | DeRocco et al. |
| 7,778,795 B2 | 8/2010 | Fukushima et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,826,981 B2 | 11/2010 | Goode, Jr. et al. |
| 7,831,310 B2 | 11/2010 | Lebel et al. |
| 7,850,621 B2 | 12/2010 | Briggs et al. |
| 7,860,574 B2 | 12/2010 | Von Arx et al. |
| 7,882,611 B2 | 2/2011 | Shah et al. |
| 7,899,511 B2 | 3/2011 | Shults et al. |
| 7,899,545 B2 | 3/2011 | John |
| 7,905,833 B2 | 3/2011 | Brister et al. |
| 7,911,010 B2 | 3/2011 | Stetter |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,954,385 B2 | 6/2011 | Raisanen |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,179,266 B2 | 5/2012 | Hermle |
| 8,192,394 B2 | 6/2012 | Estes et al. |
| 2001/0016682 A1 | 8/2001 | Berner et al. |
| 2001/0016683 A1 | 8/2001 | Darrow et al. |
| 2001/0016710 A1 | 8/2001 | Nason et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0034502 A1 | 10/2001 | Moberg et al. |
| 2001/0034617 A1 | 10/2001 | Kimata |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0053891 A1 | 12/2001 | Ackley |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0019612 A1 | 2/2002 | Watanabe et al. |
| 2002/0026937 A1 | 3/2002 | Mault |
| 2002/0027164 A1 | 3/2002 | Mault et al. |
| 2002/0028995 A1 | 3/2002 | Mault |
| 2002/0032374 A1 | 3/2002 | Holker et al. |
| 2002/0040208 A1 | 4/2002 | Flaherty et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0065682 A1 | 5/2002 | Goldenberg |
| 2002/0068858 A1 | 6/2002 | Braig et al. |
| 2002/0072784 A1 | 6/2002 | Sheppard et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | Van Antwerp et al. |
| 2002/0124017 A1 | 9/2002 | Mault |
| 2002/0133378 A1 | 9/2002 | Mault et al. |
| 2002/0161286 A1 | 10/2002 | Gerber et al. |
| 2002/0169394 A1 | 11/2002 | Eppstein et al. |
| 2002/0169439 A1 | 11/2002 | Flaherty |
| 2002/0177764 A1 | 11/2002 | Sohrab |
| 2002/0193679 A1 | 12/2002 | Malave et al. |
| 2003/0009133 A1 | 1/2003 | Ramey |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0050546 A1 | 3/2003 | Desai et al. |
| 2003/0050575 A1 | 3/2003 | Diermann et al. |
| 2003/0055380 A1 | 3/2003 | Flaherty |
| 2003/0060692 A1 | 3/2003 | Ruchti et al. |
| 2003/0060765 A1 | 3/2003 | Campbell et al. |
| 2003/0065254 A1 | 4/2003 | Schulman et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0078560 A1 | 4/2003 | Miller et al. |
| 2003/0100040 A1 | 5/2003 | Bonnacaze et al. |
| 2003/0100821 A1 | 5/2003 | Heller et al. |
| 2003/0105407 A1 | 6/2003 | Pearce, Jr. et al. |
| 2003/0107487 A1 | 6/2003 | Korman et al. |
| 2003/0108976 A1 | 6/2003 | Braig et al. |
| 2003/0118460 A1 | 6/2003 | Lilie et al. |
| 2003/0130616 A1 | 7/2003 | Steil et al. |
| 2003/0134347 A1 | 7/2003 | Heller et al. |
| 2003/0135100 A1 | 7/2003 | Kim et al. |

| | | |
|---|---|---|
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0154405 A1 | 8/2003 | Harrison |
| 2003/0158472 A1 | 8/2003 | Sohrab |
| 2003/0158707 A1 | 8/2003 | Doi |
| 2003/0167035 A1 | 9/2003 | Flaherty et al. |
| 2003/0175806 A1 | 9/2003 | Rule et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0198558 A1 | 10/2003 | Nason et al. |
| 2003/0199825 A1 | 10/2003 | Flaherty |
| 2003/0199837 A1 | 10/2003 | Vachon |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208154 A1 | 11/2003 | Close et al. |
| 2003/0208409 A1 | 11/2003 | Mault |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0214304 A1 | 11/2003 | Karinka et al. |
| 2003/0217966 A1 | 11/2003 | Tapsak et al. |
| 2003/0225360 A1 | 12/2003 | Eppstein et al. |
| 2003/0225361 A1 | 12/2003 | Sabra |
| 2003/0226695 A1 | 12/2003 | Mault |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0018486 A1 | 1/2004 | Dunn et al. |
| 2004/0019321 A1 | 1/2004 | Sage et al. |
| 2004/0027253 A1 | 2/2004 | Marsh et al. |
| 2004/0030226 A1 | 2/2004 | Quy |
| 2004/0034289 A1 | 2/2004 | Teller et al. |
| 2004/0039256 A1 | 2/2004 | Kawatahara et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0059284 A1 | 3/2004 | Nash et al. |
| 2004/0064088 A1 | 4/2004 | Gorman et al. |
| 2004/0064096 A1 | 4/2004 | Flaherty et al. |
| 2004/0064133 A1 | 4/2004 | Miller et al. |
| 2004/0072357 A1 | 4/2004 | Stiene et al. |
| 2004/0073095 A1 | 4/2004 | Causey, III et al. |
| 2004/0085215 A1 | 5/2004 | Moberg et al. |
| 2004/0096959 A1 | 5/2004 | Stiene et al. |
| 2004/0100376 A1 | 5/2004 | Lye et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0115067 A1 | 6/2004 | Rush et al. |
| 2004/0116847 A1 | 6/2004 | Wall |
| 2004/0116866 A1 | 6/2004 | Gorman et al. |
| 2004/0122353 A1 | 6/2004 | Shahmirian et al. |
| 2004/0132220 A1 | 7/2004 | Fish |
| 2004/0133092 A1 | 7/2004 | Kain |
| 2004/0152622 A1 | 8/2004 | Keith et al. |
| 2004/0153032 A1 | 8/2004 | Garribotto et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0207054 A1 | 10/2004 | Brown et al. |
| 2004/0208780 A1 | 10/2004 | Faries, Jr. et al. |
| 2004/0210184 A1 | 10/2004 | Kost et al. |
| 2004/0225338 A1 | 11/2004 | Lebel et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254434 A1 | 12/2004 | Goodnow et al. |
| 2004/0254884 A1 | 12/2004 | Haber et al. |
| 2004/0263354 A1 | 12/2004 | Mann et al. |
| 2004/0264396 A1 | 12/2004 | Ginzburg et al. |
| 2005/0003470 A1 | 1/2005 | Nelson et al. |
| 2005/0009126 A1 | 1/2005 | Andrews et al. |
| 2005/0010269 A1 | 1/2005 | Lebel et al. |
| 2005/0016276 A1 | 1/2005 | Guan et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0045476 A1 | 3/2005 | Neel et al. |
| 2005/0049473 A1 | 3/2005 | Desai et al. |
| 2005/0051580 A1 | 3/2005 | Ramey |
| 2005/0053365 A1 | 3/2005 | Adams et al. |
| 2005/0054909 A1 | 3/2005 | Petisce et al. |
| 2005/0059926 A1 | 3/2005 | Sage, Jr. et al. |
| 2005/0065464 A1 | 3/2005 | Talbot et al. |
| 2005/0090607 A1 | 4/2005 | Tapsak et al. |
| 2005/0090808 A1 | 4/2005 | Malave et al. |
| 2005/0112169 A1 | 5/2005 | Brauker et al. |
| 2005/0113653 A1 | 5/2005 | Fox et al. |
| 2005/0113657 A1 | 5/2005 | Alarcon et al. |
| 2005/0113658 A1 | 5/2005 | Jacobson et al. |
| 2005/0118726 A1 | 6/2005 | Scultz et al. |
| 2005/0121322 A1 | 6/2005 | Say et al. |
| 2005/0124873 A1 | 6/2005 | Shults et al. |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171512 A1 | 8/2005 | Flaherty |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182358 A1 | 8/2005 | Veit et al. |
| 2005/0182366 A1 | 8/2005 | Vogt et al. |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203461 A1 | 9/2005 | Flaherty et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0218880 A1 | 10/2005 | Ioffe |
| 2005/0235732 A1 | 10/2005 | Rush |

| | | | | | | |
|---|---|---|---|---|---|---|
| 2005/0236361 A1 | 10/2005 | Ufer et al. | | 2007/0055799 A1 | 3/2007 | Koehler et al. |
| 2005/0238503 A1 | 10/2005 | Rush et al. | | 2007/0078323 A1 | 4/2007 | Reggiardo et al. |
| 2005/0238507 A1 | 10/2005 | DiIanni et al. | | 2007/0078818 A1 | 4/2007 | Zvitz et al. |
| 2005/0239154 A1 | 10/2005 | Feldman et al. | | 2007/0100222 A1 | 5/2007 | Mastrototaro et al. |
| 2005/0239518 A1 | 10/2005 | D'Agostino et al. | | 2007/0106135 A1 | 5/2007 | Sloan |
| 2005/0245795 A1 | 11/2005 | Goode, Jr. et al. | | 2007/0118405 A1 | 5/2007 | Campbell et al. |
| 2005/0245799 A1 | 11/2005 | Brauker et al. | | 2007/0135697 A1 | 6/2007 | Reggiardo |
| 2005/0245839 A1 | 11/2005 | Stivoric et al. | | 2007/0153705 A1 | 7/2007 | Rosar et al. |
| 2005/0249506 A1 | 11/2005 | Fuse | | 2007/0156033 A1 | 7/2007 | Causey, III et al. |
| 2005/0249606 A1 | 11/2005 | Rush | | 2007/0156094 A1 | 7/2007 | Safabash et al. |
| 2005/0251083 A1 | 11/2005 | Carr-Brendel et al. | | 2007/0163880 A1 | 7/2007 | Woo et al. |
| 2005/0261660 A1 | 11/2005 | Choi | | 2007/0173711 A1 | 7/2007 | Shah et al. |
| 2005/0267550 A1 | 12/2005 | Hess et al. | | 2007/0176867 A1 | 8/2007 | Reggiardo et al. |
| 2005/0267780 A1 | 12/2005 | Ray et al. | | 2007/0203966 A1 | 8/2007 | Brauker et al. |
| 2005/0271546 A1 | 12/2005 | Gerber et al. | | 2007/0219480 A1 | 9/2007 | Kamen et al. |
| 2005/0271547 A1 | 12/2005 | Gerber et al. | | 2007/0219597 A1 | 9/2007 | Kamen et al. |
| 2005/0272640 A1 | 12/2005 | Doyle, III et al. | | 2007/0232880 A1 | 10/2007 | Siddiqui et al. |
| 2005/0272985 A1 | 12/2005 | Kotulla et al. | | 2007/0235331 A1 | 10/2007 | Simpson et al. |
| 2005/0277844 A1 | 12/2005 | Strother et al. | | 2007/0244383 A1 | 10/2007 | Talbot et al. |
| 2005/0287620 A1 | 12/2005 | Heller et al. | | 2007/0253021 A1 | 11/2007 | Mehta et al. |
| 2006/0001538 A1 | 1/2006 | Kraft et al. | | 2007/0255531 A1 | 11/2007 | Drew |
| 2006/0001550 A1 | 1/2006 | Mann et al. | | 2007/0258395 A1 | 11/2007 | Jollota et al. |
| 2006/0001551 A1 | 1/2006 | Kraft et al. | | 2007/0270672 A1 | 11/2007 | Hayter |
| 2006/0003398 A1 | 1/2006 | Heller et al. | | 2007/0285238 A1 | 12/2007 | Batra |
| 2006/0004271 A1 | 1/2006 | Peyser et al. | | 2008/0018433 A1 | 1/2008 | Pitt-Pladdy |
| 2006/0004603 A1 | 1/2006 | Peterka et al. | | 2008/0021666 A1 | 1/2008 | Goode, Jr. et al. |
| 2006/0007017 A1 | 1/2006 | Mann et al. | | 2008/0030369 A1 | 2/2008 | Mann et al. |
| 2006/0015020 A1 | 1/2006 | Neale et al. | | 2008/0033254 A1 | 2/2008 | Kamath et al. |
| 2006/0015024 A1 | 1/2006 | Brister et al. | | 2008/0045824 A1 | 2/2008 | Tapsak et al. |
| 2006/0016700 A1 | 1/2006 | Brister et al. | | 2008/0057484 A1 | 3/2008 | Miyata et al. |
| 2006/0017923 A1 | 1/2006 | Ruchti et al. | | 2008/0058626 A1 | 3/2008 | Miyata et al. |
| 2006/0019327 A1 | 1/2006 | Brister et al. | | 2008/0058678 A1 | 3/2008 | Miyata et al. |
| 2006/0020186 A1 | 1/2006 | Brister et al. | | 2008/0058773 A1 | 3/2008 | John |
| 2006/0020187 A1 | 1/2006 | Brister et al. | | 2008/0061961 A1 | 3/2008 | John |
| 2006/0020188 A1 | 1/2006 | Kamath et al. | | 2008/0064941 A1 | 3/2008 | Funderburk et al. |
| 2006/0020189 A1 | 1/2006 | Brister et al. | | 2008/0064943 A1 | 3/2008 | Talbot et al. |
| 2006/0020190 A1 | 1/2006 | Kamath et al. | | 2008/0071156 A1 | 3/2008 | Brister et al. |
| 2006/0020191 A1 | 1/2006 | Brister et al. | | 2008/0071328 A1 | 3/2008 | Haubrich et al. |
| 2006/0020192 A1 | 1/2006 | Brister et al. | | 2008/0083617 A1 | 4/2008 | Simpson et al. |
| 2006/0025663 A1 | 2/2006 | Talbot et al. | | 2008/0086042 A1 | 4/2008 | Brister et al. |
| 2006/0031094 A1 | 2/2006 | Cohen et al. | | 2008/0086044 A1 | 4/2008 | Brister et al. |
| 2006/0036139 A1 | 2/2006 | Brister et al. | | 2008/0086273 A1 | 4/2008 | Shults et al. |
| 2006/0036140 A1 | 2/2006 | Brister et al. | | 2008/0097918 A1 | 4/2008 | Spector et al. |
| 2006/0036141 A1 | 2/2006 | Kamath et al. | | 2008/0103447 A1 | 5/2008 | Reggiardo et al. |
| 2006/0036142 A1 | 2/2006 | Brister et al. | | 2008/0108942 A1 | 5/2008 | Brister et al. |
| 2006/0036143 A1 | 2/2006 | Brister et al. | | 2008/0119703 A1 | 5/2008 | Brister et al. |
| 2006/0036144 A1 | 2/2006 | Brister et al. | | 2008/0119705 A1 | 5/2008 | Patel et al. |
| 2006/0036145 A1 | 2/2006 | Brister et al. | | 2008/0139910 A1 | 6/2008 | Mastrototaro et al. |
| 2006/0036187 A1 | 2/2006 | Vos et al. | | 2008/0167572 A1 | 7/2008 | Stivoric et al. |
| 2006/0040402 A1 | 2/2006 | Brauker et al. | | 2008/0183061 A1 | 7/2008 | Goode et al. |
| 2006/0041229 A1 | 2/2006 | Garibotto et al. | | 2008/0183399 A1 | 7/2008 | Goode et al. |
| 2006/0052679 A1 | 3/2006 | Kotulla et al. | | 2008/0188731 A1 | 8/2008 | Brister et al. |
| 2006/0058602 A1 | 3/2006 | Kwiatkowski et al. | | 2008/0189051 A1 | 8/2008 | Goode et al. |
| 2006/0058627 A1 | 3/2006 | Flaherty et al. | | 2008/0194935 A1 | 8/2008 | Brister et al. |
| 2006/0063218 A1 | 3/2006 | Bartkowiak et al. | | 2008/0194936 A1 | 8/2008 | Goode et al. |
| 2006/0074564 A1 | 4/2006 | Bartkowiak et al. | | 2008/0194937 A1 | 8/2008 | Goode et al. |
| 2006/0094986 A1 | 5/2006 | Neel et al. | | 2008/0194938 A1 | 8/2008 | Brister et al. |
| 2006/0154642 A1 | 7/2006 | Scannell | | 2008/0195049 A1 | 8/2008 | Thalmann et al. |
| 2006/0161078 A1 | 7/2006 | Schraga | | 2008/0195232 A1 | 8/2008 | Carr-Brendel et al. |
| 2006/0166629 A1 | 7/2006 | Reggiardo | | 2008/0195967 A1 | 8/2008 | Goode et al. |
| 2006/0173259 A1 | 8/2006 | Flaherty et al. | | 2008/0197024 A1 | 8/2008 | Simpson et al. |
| 2006/0173444 A1 | 8/2006 | Choy et al. | | 2008/0200788 A1 | 8/2008 | Brister et al. |
| 2006/0173712 A1 | 8/2006 | Joubert | | 2008/0200789 A1 | 8/2008 | Brister et al. |
| 2006/0178633 A1 | 8/2006 | Garibotto et al. | | 2008/0200791 A1 | 8/2008 | Simpson et al. |
| 2006/0202805 A1 | 9/2006 | Schulman et al. | | 2008/0200838 A1 | 8/2008 | Goldberger et al. |
| 2006/0222566 A1 | 10/2006 | Brauker et al. | | 2008/0208025 A1 | 8/2008 | Shults et al. |
| 2006/0224141 A1 | 10/2006 | Rush et al. | | 2008/0214915 A1 | 9/2008 | Brister et al. |
| 2006/0240403 A1 | 10/2006 | List et al. | | 2008/0214918 A1 | 9/2008 | Brister et al. |
| 2006/0247508 A1 | 11/2006 | Fennell | | 2008/0228051 A1 | 9/2008 | Shults et al. |
| 2006/0247710 A1 | 11/2006 | Goetz et al. | | 2008/0228054 A1 | 9/2008 | Shults et al. |
| 2006/0253085 A1 | 11/2006 | Geismar et al. | | 2008/0228055 A1 | 9/2008 | Sher |
| 2006/0253086 A1 | 11/2006 | Moberg et al. | | 2008/0235469 A1 | 9/2008 | Drew |
| 2006/0273759 A1 | 12/2006 | Reggiardo | | 2008/0242961 A1 | 10/2008 | Brister et al. |
| 2006/0282290 A1 | 12/2006 | Flaherty et al. | | 2008/0255438 A1 | 10/2008 | Saidara et al. |
| 2006/0287691 A1 | 12/2006 | Drew | | 2008/0262469 A1 | 10/2008 | Brister et al. |
| 2006/0293577 A1 | 12/2006 | Morrison et al. | | 2008/0275313 A1 | 11/2008 | Brister et al. |
| 2007/0007133 A1 | 1/2007 | Mang et al. | | 2008/0287764 A1 | 11/2008 | Rasdal et al. |
| 2007/0016381 A1 | 1/2007 | Kamath et al. | | 2008/0287765 A1 | 11/2008 | Rasdal et al. |
| 2007/0032717 A1 | 2/2007 | Brister et al. | | 2008/0287766 A1 | 11/2008 | Rasdal et al. |

| | | | | | | |
|---|---|---|---|---|---|---|
| 2008/0296155 A1 | 12/2008 | Shults et al. | | 2009/0299156 A1 | 12/2009 | Simpson et al. |
| 2008/0306368 A1 | 12/2008 | Goode et al. | | 2009/0299162 A1 | 12/2009 | Brauker et al. |
| 2008/0306434 A1 | 12/2008 | Dobbles et al. | | 2009/0299276 A1 | 12/2009 | Brauker et al. |
| 2008/0306435 A1 | 12/2008 | Kamath et al. | | 2010/0010324 A1 | 1/2010 | Brauker et al. |
| 2008/0306444 A1 | 12/2008 | Brister et al. | | 2010/0010331 A1 | 1/2010 | Brauker et al. |
| 2008/0312518 A1 | 12/2008 | Jina et al. | | 2010/0010332 A1 | 1/2010 | Brauker et al. |
| 2009/0005666 A1 | 1/2009 | Shin et al. | | 2010/0016687 A1 | 1/2010 | Brauker et al. |
| 2009/0012379 A1 | 1/2009 | Goode et al. | | 2010/0016698 A1 | 1/2010 | Rasdal et al. |
| 2009/0018424 A1 | 1/2009 | Kamath et al. | | 2010/0022855 A1 | 1/2010 | Brauker et al. |
| 2009/0030294 A1 | 1/2009 | Petisce et al. | | 2010/0030038 A1 | 2/2010 | Brauker et al. |
| 2009/0036758 A1 | 2/2009 | Brauker et al. | | 2010/0030053 A1 | 2/2010 | Goode, Jr. et al. |
| 2009/0036763 A1 | 2/2009 | Brauker et al. | | 2010/0030484 A1 | 2/2010 | Brauker et al. |
| 2009/0043181 A1 | 2/2009 | Brauker et al. | | 2010/0030485 A1 | 2/2010 | Brauker et al. |
| 2009/0043182 A1 | 2/2009 | Brauker et al. | | 2010/0036215 A1 | 2/2010 | Goode, Jr. et al. |
| 2009/0043525 A1 | 2/2009 | Brauker et al. | | 2010/0036216 A1 | 2/2010 | Goode, Jr. et al. |
| 2009/0043541 A1 | 2/2009 | Brauker et al. | | 2010/0036222 A1 | 2/2010 | Goode, Jr. et al. |
| 2009/0043542 A1 | 2/2009 | Brauker et al. | | 2010/0036223 A1 | 2/2010 | Goode, Jr. et al. |
| 2009/0045055 A1 | 2/2009 | Rhodes et al. | | 2010/0036225 A1 | 2/2010 | Goode, Jr. et al. |
| 2009/0062633 A1 | 3/2009 | Brauker et al. | | 2010/0041971 A1 | 2/2010 | Goode, Jr. et al. |
| 2009/0062635 A1 | 3/2009 | Brauker et al. | | 2010/0045465 A1 | 2/2010 | Brauker et al. |
| 2009/0063196 A1 | 3/2009 | Frederickson | | 2010/0049024 A1 | 2/2010 | Saint et al. |
| 2009/0063402 A1 | 3/2009 | Hayter | | 2010/0063373 A1 | 3/2010 | Kamath et al. |
| 2009/0068954 A1 | 3/2009 | Reggiardo et al. | | 2010/0076283 A1 | 3/2010 | Simpson et al. |
| 2009/0069750 A1 | 3/2009 | Schraga | | 2010/0081908 A1 | 4/2010 | Dobbles et al. |
| 2009/0076356 A1 | 3/2009 | Simpson et al. | | 2010/0081910 A1 | 4/2010 | Brister et al. |
| 2009/0076358 A1 | 3/2009 | Reggiardo et al. | | 2010/0087724 A1 | 4/2010 | Brauker et al. |
| 2009/0076360 A1 | 3/2009 | Brister et al. | | 2010/0096259 A1 | 4/2010 | Zhang et al. |
| 2009/0076361 A1 | 3/2009 | Kamath et al. | | 2010/0099970 A1 | 4/2010 | Shults et al. |
| 2009/0083003 A1 | 3/2009 | Reggiardo et al. | | 2010/0099971 A1 | 4/2010 | Shults et al. |
| 2009/0085768 A1 | 4/2009 | Patel et al. | | 2010/0119693 A1 | 5/2010 | Tapsak et al. |
| 2009/0099436 A1 | 4/2009 | Brister et al. | | 2010/0121169 A1 | 5/2010 | Petisce et al. |
| 2009/0105554 A1 | 4/2009 | Stahmann et al. | | 2010/0190435 A1 | 7/2010 | Cook et al. |
| 2009/0112478 A1 | 4/2009 | Mueller, Jr. et al. | | 2010/0241447 A1 | 9/2010 | Siniaguine et al. |
| 2009/0124877 A1 | 5/2009 | Goode, Jr. et al. | | 2011/0004276 A1 | 1/2011 | Blair et al. |
| 2009/0124878 A1 | 5/2009 | Goode et al. | | 2011/0152637 A1 | 6/2011 | Kateraas et al. |
| 2009/0124879 A1 | 5/2009 | Brister et al. | | | | |
| 2009/0124964 A1 | 5/2009 | Leach et al. | | FOREIGN PATENT DOCUMENTS | | |
| 2009/0131768 A1 | 5/2009 | Simpson et al. | | CA | 2413148 | 8/2010 |
| 2009/0131769 A1 | 5/2009 | Leach et al. | | EP | 0455455 | 11/1991 |
| 2009/0131776 A1 | 5/2009 | Simpson et al. | | EP | 0465708 | 1/1992 |
| 2009/0131777 A1 | 5/2009 | Simpson et al. | | EP | 0518524 | 12/1992 |
| 2009/0137886 A1 | 5/2009 | Shariati et al. | | EP | 0724859 | 8/1996 |
| 2009/0137887 A1 | 5/2009 | Shariati et al. | | EP | 0878707 | 11/1998 |
| 2009/0143659 A1 | 6/2009 | Li et al. | | EP | 0678308 | 5/2000 |
| 2009/0143660 A1 | 6/2009 | Brister et al. | | EP | 0543916 | 7/2001 |
| 2009/0150186 A1 | 6/2009 | Cohen et al. | | EP | 1130638 | 9/2001 |
| 2009/0156919 A1 | 6/2009 | Brister et al. | | EP | 0980688 | 12/2002 |
| 2009/0156924 A1 | 6/2009 | Shariati et al. | | EP | 1292218 | 3/2003 |
| 2009/0163790 A1 | 6/2009 | Brister et al. | | EP | 1077634 | 7/2003 |
| 2009/0163791 A1 | 6/2009 | Brister et al. | | EP | 1755443 | 11/2005 |
| 2009/0178459 A1 | 7/2009 | Li et al. | | EP | 1666091 | 6/2006 |
| 2009/0182217 A1 | 7/2009 | Li et al. | | EP | 1703697 | 9/2006 |
| 2009/0189738 A1 | 7/2009 | Hermle | | EP | 1704893 | 9/2006 |
| 2009/0192366 A1 | 7/2009 | Mensinger et al. | | EP | 1783536 | 5/2007 |
| 2009/0192380 A1 | 7/2009 | Shariati et al. | | EP | 1897487 | 11/2009 |
| 2009/0192722 A1 | 7/2009 | Shariati et al. | | EP | 1897492 | 11/2009 |
| 2009/0192724 A1 | 7/2009 | Brauker et al. | | EP | 2113864 | 11/2009 |
| 2009/0192745 A1 | 7/2009 | Kamath et al. | | EP | 1897488 | 12/2009 |
| 2009/0192751 A1 | 7/2009 | Kamath et al. | | EP | 1681992 | 4/2010 |
| 2009/0203981 A1 | 8/2009 | Brauker et al. | | EP | 1448489 | 8/2010 |
| 2009/0204341 A1 | 8/2009 | Brauker et al. | | EP | 1971396 | 8/2010 |
| 2009/0216103 A1 | 8/2009 | Brister et al. | | EP | 2153382 | 2/2012 |
| 2009/0216553 A1 | 8/2009 | Cellura | | EP | 2284773 | 2/2012 |
| 2009/0234200 A1 | 9/2009 | Husheer | | JP | 2001-177423 | 6/2001 |
| 2009/0240120 A1 | 9/2009 | Mensinger et al. | | JP | 2001-056673 | 11/2001 |
| 2009/0240128 A1 | 9/2009 | Mensinger et al. | | WO | WO-96/14026 | 5/1996 |
| 2009/0240193 A1 | 9/2009 | Mensinger et al. | | WO | WO-97/33513 | 9/1997 |
| 2009/0242399 A1 | 10/2009 | Kamath et al. | | WO | WO-99/22236 | 5/1999 |
| 2009/0242425 A1 | 10/2009 | Kamath et al. | | WO | WO-99/56613 | 11/1999 |
| 2009/0247855 A1 | 10/2009 | Boock et al. | | WO | WO-00/74753 | 12/2000 |
| 2009/0247856 A1 | 10/2009 | Boock et al. | | WO | WO-01/52727 | 7/2001 |
| 2009/0247931 A1 | 10/2009 | Damgaard-Sorensen | | WO | WO-01/54753 | 8/2001 |
| 2009/0267765 A1 | 10/2009 | Greene et al. | | WO | WO-01/71186 | 9/2001 |
| 2009/0287073 A1 | 11/2009 | Boock et al. | | WO | WO-02/39086 | 5/2002 |
| 2009/0287074 A1 | 11/2009 | Shults et al. | | WO | WO-02/084860 | 10/2002 |
| 2009/0289796 A1 | 11/2009 | Blumberg | | WO | WO-02/100263 | 12/2002 |
| 2009/0299155 A1 | 12/2009 | Yang et al. | | WO | WO-02/100469 | 12/2002 |

| | | |
|---|---|---|
| WO | WO-03/006091 | 1/2003 |
| WO | WO-03/053503 | 7/2003 |
| WO | WO-2004/028337 | 4/2004 |
| WO | WO-2004/032994 | 4/2004 |
| WO | WO-2004/061420 | 7/2004 |
| WO | WO-2005/045744 | 5/2005 |
| WO | WO-2005/089103 | 9/2005 |
| WO | WO-2005/101994 | 11/2005 |
| WO | WO-2006/003919 | 1/2006 |
| WO | WO-2006/032653 | 3/2006 |
| WO | WO-2006/079114 | 7/2006 |
| WO | WO-2006/086701 | 8/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/124099 | 11/2006 |
| WO | WO-2006/132884 | 12/2006 |
| WO | WO-2007/041072 | 4/2007 |
| WO | WO-2007/090037 | 8/2007 |
| WO | WO-2008/055037 | 5/2008 |
| WO | WO-2008/086541 | 7/2008 |
| WO | WO-2008/110267 | 9/2008 |
| WO | WO-2011/022418 | 2/2011 |

OTHER PUBLICATIONS

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

U.S. Appl. No. 10/832,512, Notice of Allowance mailed Dec. 31, 2009.

U.S. Appl. No. 10/832,512, Office Action mailed Mar. 26, 2009.

U.S. Appl. No. 10/832,512, Office Action mailed Aug. 13, 2008.

U.S. Appl. No. 10/832,512, Office Action mailed Nov. 14, 2007.

U.S. Appl. No. 10/832,512, Office Action mailed Feb. 27, 2007.

U.S. Appl. No. 10/832,512, Office Action mailed Feb. 16, 2006.

U.S. Appl. No. 10/832,512, Office Action mailed Aug. 2, 2006.

U.S. Appl. No. 10/832,512, Office Action mailed Jun. 2, 2005.

U.S. Appl. No. 10/832,512, Advisory Action mailed Oct. 29, 2008.

* cited by examiner

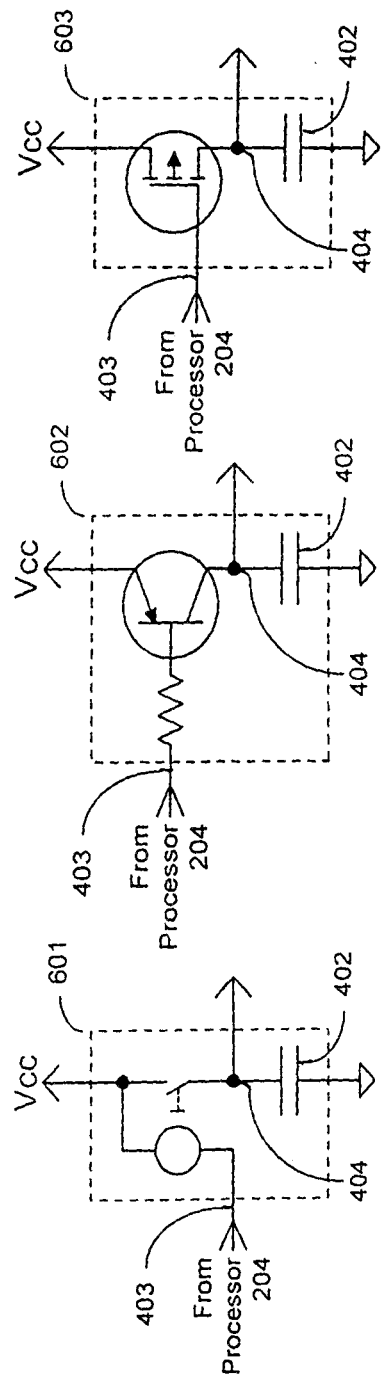

METHOD AND APPARATUS FOR PROVIDING PEAK DETECTION CIRCUITRY FOR DATA COMMUNICATION SYSTEMS

RELATED APPLICATIONS

This application is a continuation application of U.S. patent application Ser. No. 10/832,512 filed Apr. 27, 2004, now U.S. Pat. No. 7,679,407, which claims priority under 35 USC §119(e) to U.S. Provisional Application No. 60/466,243 filed Apr. 28, 2003 entitled "Method and Apparatus for Providing Peak Detection Circuitry for Data Communication Systems", the disclosures of each of which are incorporated herein by reference for all purposes.

BACKGROUND

The present invention relates to communication systems. More specifically, the present invention relates to radio frequency (RF) communication systems for data communication between portable electronic devices such as in continuous glucose monitoring systems.

Continuous glucose monitoring systems generally include a small, lightweight battery powered and microprocessor controlled system which is configured to detect signals proportional to the corresponding measured glucose levels using an electrometer, and RF signals to transmit the collected data. When the microprocessor is active or when the system is in the process of processing or transmitting data, the battery power supply may display a loading effect commonly referred to as "drooping" due to the current consumption of the microprocessor operation or the transmit function compared to the average current draw level.

The voltage drooping may occur when the processor (or controller) for the transmitter initiates and performs a configured procedure, or alternatively, in the case where the RF transmitter initiates data transmission. For example, the processor may draw a small amount of current in idle state (for example, 1 μA), while in active processing mode, it may draw as much as 2 mA. Additionally, the RF transmitter may draw approximately 10 mA during data transmission state.

The drooping effect is particularly prominent after a portion of the available battery energy has been consumed (that is, the battery energy is partially discharged) and is typical for small batteries where size, weight and power density are optimized versus peak current capacity. This, in turn, may have a negative impact on the processing of detected signals such as by signal degradation or data loss, and importantly, may adversely affect the delicate electrometer and the analog circuitry in the transmitter unit of the monitoring system. More specifically, when the analog front end circuitry in the transmitter of the monitoring system is disturbed, there may be a several second delay when the data may be unusable and a longer delay (for example, on the order of 10 seconds) when the data may be unreliable or beyond the tolerance range of desired accuracy.

In view of the foregoing, it would be desirable to isolate the delicate electrometer and the analog circuitry of the monitoring system, for example, in the transmitting side, from the adverse effects of battery voltage drooping using simple, low cost and low noise approaches, in contrast to the existing techniques using, for example, a DC to DC converter which typically has higher cost as well as higher noise.

SUMMARY OF THE INVENTION

Accordingly, in one embodiment of the present invention, there is provided a peak detection circuit comprising a diode including an input terminal and an output terminal the input terminal of the diode configured to receive an input signal, a capacitor operatively coupled to the output terminal of the diode, and an output terminal operatively coupled to the capacitor and the output terminal of the diode for outputting an output signal.

The diode may include a Schottky diode switch, and further, the input signal may include a voltage signal from a power supply.

Moreover, in one embodiment, a voltage droop may be detected at the input terminal of the diode, and where the diode and the capacitor may be configured to compensate for the voltage droop.

In a further embodiment of the present invention, there is provided a data communication system including peak detection circuit comprising a peak detection circuit configured to receive a power supply signal, and further to output a detected signal, and a low pass filter operatively coupled to the detection circuit, the detection circuit configured to receive the detected signal, where the peak detection circuit may be configured to detect a voltage droop in the power supply signal and further, to compensate for the voltage droop.

In a further embodiment, the peak detection circuit may be configured to electrically isolate the detected voltage droop.

Additionally, the peak detection circuit may in an alternate embodiment include a passive switching configuration.

Also, the peak detection circuit may in one embodiment include a diode operatively coupled to a capacitance, where the diode may include a Schottky diode switch.

In accordance with yet another embodiment of the present invention, there is provided a method of providing a peak detection circuit, comprising the steps of providing a diode having an input terminal and an output terminal the input terminal of the diode configured to receive an input signal, operatively coupling a capacitor to the output terminal of the diode, and operatively coupling an output terminal to the capacitor and the output terminal of the diode for outputting an output signal.

Also, the input signal may include a voltage signal from a power supply.

Moreover, in a further embodiment, the method may further include the steps of detecting a voltage droop at the input terminal of the diode, and compensating for the voltage droop by the diode and the capacitor.

In accordance with still another embodiment of the present invention, there is provided a method of providing peak detection in a data communication system, comprising the steps of configuring a peak detection circuit to detect a voltage droop in a power supply signal and to output a compensated signal, low pass filtering the compensated signal from the peak detection circuit.

In one embodiment, the step of configuring the peak detection circuit may further include the step of electrically isolating the detected voltage droop.

Moreover, the step of providing the peak detection circuit may include providing a passive switching configuration.

Additionally, the step of configuring the peak detection circuit may include the step of operatively coupling a diode to a capacitance.

Indeed, in accordance with the various embodiments of the present invention, there is provided a peak detection circuit in the transmitter of a data communication system which is configured to detect a voltage droop from its power supply such as a battery configured to power the transmitter, and to effectively compensate for the detected voltage signal droop such that the delicate circuitry of the electrometer and the analog front end circuitry of the transmitter unit may be electrically isolated (for example, by switching off the connection between the electrometer and the analog front end circuitry, and the power supply source) from the detected voltage drooping while the necessary current is drawn from another source such as a capacitor to support the required voltage level of the electrometer and the analog front end circuitry.

The peak detection circuit in one aspect may include passive switching configurations with a diode and a capacitor combination. In addition, a low pass filter may be operatively coupled to the peak detection circuit to filter out any switching noise transients. In an alternate embodiment, the peak detection circuit may include active components such as a relay switch, a BJT or FET transistor switch. In this case, the switching mechanism is controlled by the processor to turn the switch on or off, in case of power supply voltage drooping, as opposed to the passive component configuration with the diode, in which case such voltage drooping is automatically detected and the switching mechanism of the peak detection circuit accordingly operated in response thereto.

Furthermore, as discussed above, the diode used for the peak detection circuit may include a Schottky diode switch. Moreover, the peak detection circuit in one embodiment may be provided between the power supply and the analog front end circuitry of the transmitter unit in the continuous glucose monitoring system such that in the case where power supply voltage drooping occurs, the peak detection circuit may be configured to isolate the delicate circuitry of the analog front end of the transmitter unit from the power supply, and rather allow the electrometer and the analog front end circuitry of the transmitter to draw the necessary power from a capacitor of the peak detection circuit to ensure continuous and proper operation.

Accordingly, in accordance with the various embodiments of the present invention, by using a peak detection circuit with a tuned low pass filter, an effective, low cost and low noise approach to isolating the battery droop, even that in excess of 0.5 volts, may be achieved such that in the monitoring system discussed above, the detected and processed data values are not substantially effected, and the delicate analog circuitry of the transmitter is not adversely affected by the fluctuation in power supply signal.

INCORPORATION BY REFERENCE

Applicants herein incorporate by reference application Ser. No. 09/753,746 filed on Jan. 2, 2001 entitled "Analyte Monitoring Device and Methods of Use", and Application No. 60/437,374 filed Dec. 31, 2002 entitled "Continuous Glucose Monitoring System and Methods of Use" each assigned to the Assignee of the present application for all purposes.

BRIEF DESCRIPTION OF THE DRAWINGS

FIGS. 6A-6C illustrate the peak detection circuits implemented using active components in accordance with several alternate embodiments of the present invention.

DETAILED DESCRIPTION

Figure 1:
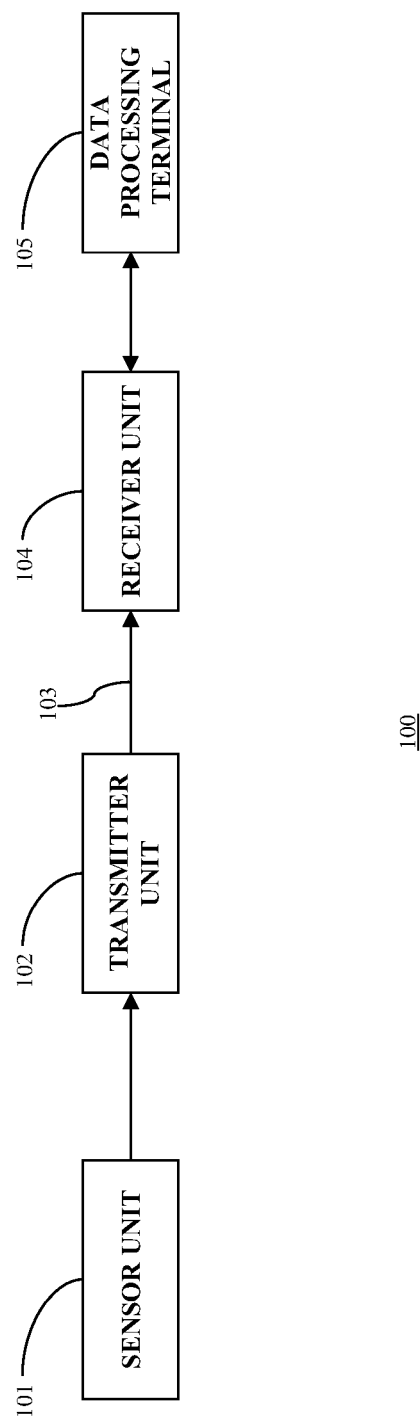
FIG. 1 illustrates a block diagram of an overall communication system for practicing one embodiment of the present invention.

FIG. 1 illustrates a data communication system such as, for example, a continuous glucose monitoring system 100 in accordance with one embodiment of the present invention. In such an embodiment, the continuous glucose monitoring system 100 includes a sensor 101, a transmitter 102 coupled to the sensor 101, and a receiver 104 which is configured to communicate with the transmitter 102 via a communication link 103. The receiver 104 may be further configured to transmit data to a data processing terminal 105 for evaluating the data received by the receiver 104. Only one sensor 101, transmitter 102, communication link 103, receiver 104, and data processing terminal 105 are shown in the embodiment of the continuous glucose monitoring system 100 illustrated in FIG. 1. However, it will be appreciated by one of ordinary skill in the art that the continuous glucose monitoring system 100 may include one or more sensor 101, transmitter 102, communication link 103, receiver 104, and data processing terminal 105, where each receiver 104 is uniquely synchronized with a respective transmitter 102.

In one embodiment of the present invention, the sensor 101 is physically positioned on the body of a user whose glucose level is being monitored. The sensor 101 is configured to continuously sample the glucose level of the user and convert the sampled glucose level into a corresponding data signal for transmission by the transmitter 102. In one embodiment, the transmitter 102 is mounted on the sensor 101 so that both devices are positioned on the user's body. The transmitter 102 performs data processing such as filtering and encoding on data signals, each of which corresponds to a sampled glucose level of the user, for transmission to the receiver 104 via the communication link 103.

In one embodiment, the continuous glucose monitoring system 100 is configured as a one-way RF communication path from the transmitter 102 to the receiver 104. In such embodiment, the transmitter 102 transmits the sampled data signals received from the sensor 101 without acknowledgement from the receiver 104 that the transmitted sampled data signals have been received. For example, the transmitter 102 may be configured to transmit the encoded sampled data signals at a fixed rate (e.g., at one minute intervals) after the completion of the initial power on procedure. Likewise, the receiver 104 may be configured to detect such transmitted encoded sampled data signals at predetermined time intervals. Alternatively, in accordance with a further embodiment of the present invention, the continuous glucose monitoring system 100 may be configured with a two-way RF communication path between the transmitter 102 and the receiver 104 using transceivers.

Additionally, in one aspect, the receiver 104 may include two sections. The first section is an analog interface section that is configured to communicate with the transmitter 102 via the communication link 103. In one embodiment, the analog interface section may include an RF receiver and an antenna for receiving and amplifying the data signals from the transmitter 102, which are thereafter, demodulated with a local oscillator and filtered through a band-pass filter. The second section of the receiver 104 is a data processing section which is configured to process the data signals received from the transmitter 102 such as by performing data decoding, error detection and correction, data clock generation, and data bit recovery.

In operation, upon completing the power-on procedure, the receiver 104 is configured to detect the presence of the transmitter 102 within its range based on, for example, the strength of the detected data signals received from the transmitter 102 or a predetermined transmitter identification information. Upon successful synchronization with the corresponding transmitter 102, the receiver 104 is configured to begin receiving from the transmitter 102 data signals corresponding to the user's detected glucose level. More specifically, the receiver 104 in one embodiment is configured to perform synchronized time hopping with the corresponding synchronized transmitter 102 via the communication link 103 to obtain the user's detected glucose level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected glucose level of the user.

Figure 2:
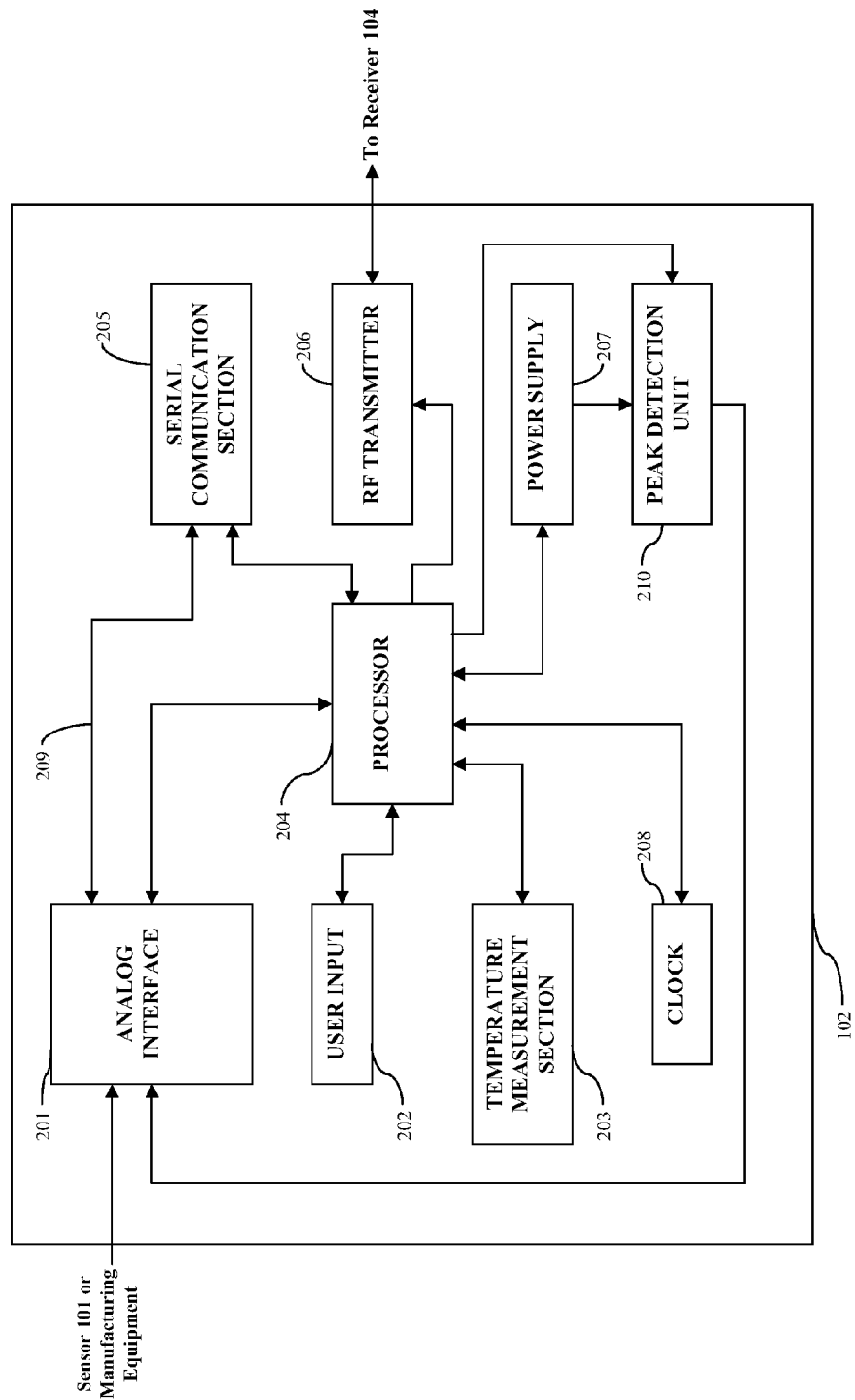
FIG. 2 is a block diagram of the transmitter of the overall communication system shown in FIG. 1 in accordance with one embodiment of the present invention.

FIG. 2 is a block diagram of the transmitter of the overall communication system shown in FIG. 1 in accordance with one embodiment of the present invention. Referring to the Figure, the transmitter 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). Further shown in FIG. 2 are a transmitter serial communication section 205 and an RF transmitter 206, each of which is also operatively coupled to the transmitter processor 204. Moreover, a power supply 207 such as a battery is also provided in the transmitter 102 to provide the necessary power for the transmitter 102. Additionally, as can be seen from the Figure, clock 208 is provided to, among others, supply real time information to the transmitter processor 204. Also shown in FIG. 2 is a peak detection unit 210 operatively coupled to the analog interface 201, the processor 204 and the power supply 207.

In one embodiment, a unidirectional input path is established from the sensor 101 (FIG. 1) and/or manufacturing and testing equipment to the analog interface 201 of the transmitter 102, while a unidirectional output is established from the output of the RF transmitter 206 of the transmitter 102 for transmission to the receiver 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter 102 is configured to transmit to the receiver 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter 102 for operation upon completion of the manufacturing process as well as for direct communication for diagnostic and testing purposes.

As discussed above, the transmitter processor 204 is configured to transmit control signals to the various sections of the transmitter 102 during the operation of the transmitter 102. In one embodiment, the transmitter processor 204 also includes a memory (not shown) for storing data such as the identification information for the transmitter 102, as well as the data signals received from the sensor 101. The stored information may be retrieved and processed for transmission to the receiver 104 under the control of the transmitter processor 204. Furthermore, the power supply 207 may include a commercially available battery.

The transmitter 102 is also configured such that the power supply section 207 is capable of providing power to the transmitter for a minimum of three months of continuous operation after having been stored for 18 months in a low-power (non-operating) mode. In one embodiment, this may be achieved by the transmitter processor 204 operating in low power modes in the non-operating state, for example, drawing no more than approximately 1 µA of current. Indeed, in one embodiment, the final step during the manufacturing process of the transmitter 102 may place the transmitter 102 in the lower power, non-operating state (i.e., post-manufacture sleep mode). In this manner, the shelf life of the transmitter 102 may be significantly improved.

Referring yet again to FIG. 2, the temperature detection section 203 of the transmitter 102 is configured to monitor the temperature of the skin near the sensor insertion site. The temperature reading is used to adjust the glucose readings obtained from the analog interface 201. The RF transmitter 206 of the transmitter 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver 104.

Additional detailed description of the continuous glucose monitoring system, its various components including the functional descriptions of the transmitter are provided in application Ser. No. 09/753,746 filed on Jan. 2, 2001 entitled "Analyte Monitoring Device and Methods of Use", and in application No. 60/437,374 filed Dec. 31, 2002 entitled "Continuous Glucose Monitoring System and Methods of Use", each assigned to the Assignee of the present application, and the disclosures of each of which are incorporated herein by reference for all purposes.

Figure 3:
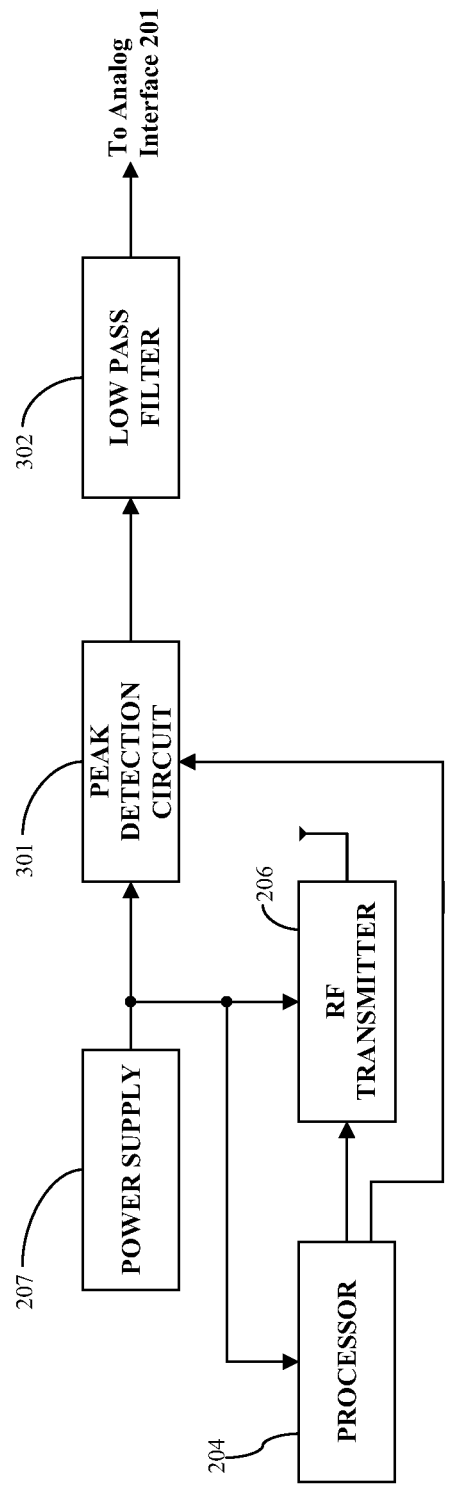
FIG. 3 is a block diagram illustrating the peak detection system in the transmitter of FIG. 2 in accordance with one embodiment of the present invention.

FIG. 3 is a block diagram illustrating the peak detection unit 210 in the transmitter of FIG. 2 in accordance with embodiment of the present invention. Referring to the Figure, there is shown a peak detection circuit 301 operatively coupled between the power supply 207 and a low pass filter 302. As further shown in FIG. 3, the power supply 207 is further operatively coupled to the processor 204 and the RF transmitter 206. The low pass filter 302 is additionally operatively coupled to the analog interface 201 (FIG. 2) which includes delicate circuitry for detecting and processing signals corresponding to the glucose level detected by the sensor unit 101 (FIG. 1), and powered by the power supply 207.

The processor 204 may draw a small amount of current in idle state (for example, 1 µA) as described above, while in active processing mode, the processor 204 may draw as much as 2 mA of current. Additionally, the RF transmitter 206 may draw approximately 10 mA of current during data transmission state. Either case of the processor 204 in active processing mode or the RF transmitter 206 in data transmission mode may result in voltage drooping from the power supply 207.

Accordingly, the peak detection circuit 301 in accordance with one embodiment is configured to detect the occurrences of the power supply voltage drooping, and to switch off the connection of the power supply 207 to the analog interface 201. In this case, the analog interface 201 may be configured to draw the necessary current from, for example, a capacitor of the peak detection circuit 301 to support the voltage necessary for operation. This will be discussed in further detail below in conjunction with the embodiments illustrated in FIGS. 4 and 5A-5C. Additionally, the low pass filter 302 in one embodiment may be configured to filter out any resulting switching noise transients also discussed in further detail below.

Figure 4:
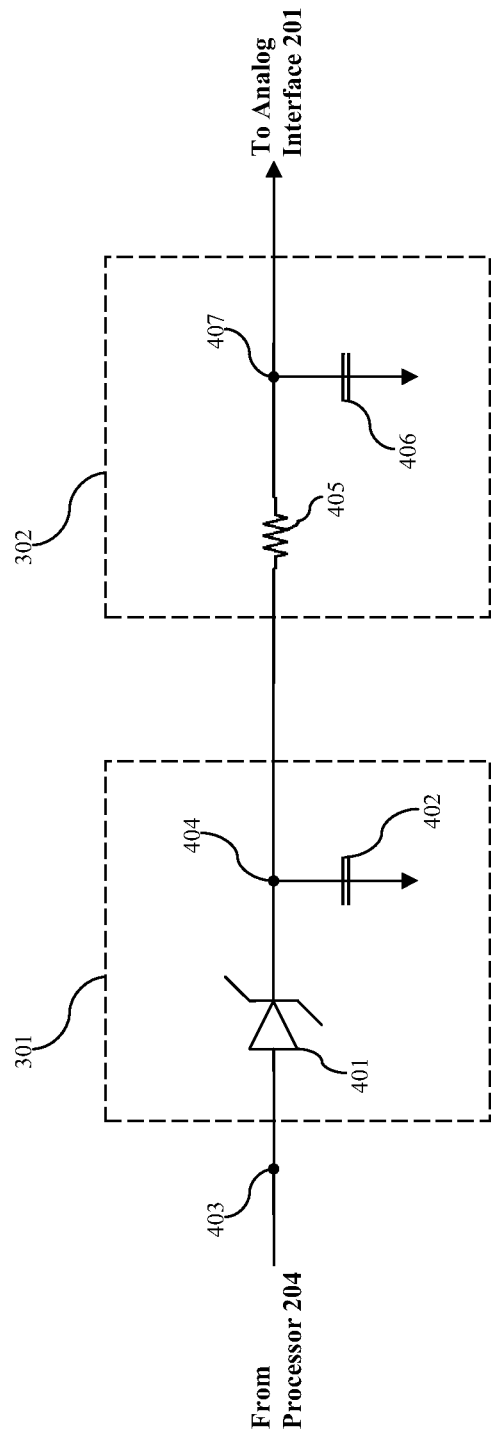
FIG. 4 illustrates the peak detection circuit and the low pass filter of the peak detection system shown in FIG. 3 in accordance with one embodiment of the present invention.

FIG. 4 illustrates the peak detection circuit and the low pass filter of the peak detection unit shown in FIG. 3 in accordance with one embodiment of the present invention. Referring to the Figure, the peak detection circuit 301 in one embodiment includes a diode 401 operatively coupled to a capacitor 402. The diode in one embodiment may be a Schottky diode configured to operate as a switch, while the capacitor 402 may, in one embodiment, have a value of approximately 10 µFarads.

Referring back to FIG. 4, the low pass filter 302 in one embodiment may include a resistor 405 operatively coupled between the peak detection circuit 301 and the interface to the analog front end circuitry, and a capacitor 406 further operatively coupled to the resistor 405. In one embodiment, the resistor 405 may have a value of 1 kOhms, while the capacitor 406 may have a value of approximately 1 µFarads. In this manner, the configuration of the resistor 405 and the capacitor 406 effectively establishes a low pass RC filter.

Referring again to FIG. 4, while any suitable diode may be used for diode 401 in the peak detection circuit 301, the Schottky diode as shown in the Figure may be used to take advantage of its properties including a lower forward voltage drop as compared to conventional diodes. This, in turn, allows the capacitor 402 of the peak detection circuit 301 to charge to a higher value, as there is a smaller voltage drop from the voltage at the input terminal 403 and the output terminal 404 of the peak detection circuit 301 under steady state conditions. In accordance with one embodiment of the present invention, the low pass RC filter 302 shown in the Figure may be implemented for each chip connected to the power supply of the analog front end circuitry.

Furthermore, in one embodiment, the diode 401 of the peak detection circuit 301 may be directly coupled to the battery or to a switched power supply source (for example, power supply 207 (FIGS. 2 and 3)). Also, the output of the processor 204 in one aspect may be used to drive the diode 401 of the peak detection circuit 301 such that the analog front end circuitry may be switched off to increase the storage (for example, post manufacture sleep mode) period when the system is being transported to the users. This approach is possible when the processor 204 output drive signal level is sufficient to power the analog front end circuitry with no noticeable output voltage droop due to loading.

Additionally, it should be noted that the low pass filter 302 in one embodiment may be configured to prevent the high frequency switching noise of the processor 204 from adversely affecting the analog front end circuitry. More specifically, since the processor 204 displays high frequency switching noise on the order of 1 MHz, a low pass filter with a cut-off frequency of, for example, 1 kHz would reduce the switching noise to approximately 0.1% or less. For example, with a 1 kOhm resistor 405 and a 1 µFarad capacitor 406 forming the low pass filter 302, the cut-off frequency is established at 1 kHz such that any signal of higher frequency than the cut-off frequency will be attenuated. In one embodiment, the low pass filter values (i.e., the values of the resistor 405 and the capacitor 406) may be varied or optimized for a given processor 204 and circuit implementation.

In the manner described above, in accordance with one embodiment of the present invention, the peak detection circuit 301 and the low pass filter 302 may be configured to provide an effective safeguard against any potential perturbation in the outputs of any circuitry operatively coupled to the analog front end circuitry (e.g., at terminal 407 shown in FIG. 4) resulting from voltage drooping of the power supply 207. In the case of the continuous glucose monitoring system discussed above, this translates to less than one least significant bit (lsb) of data change on the electrometer output as measured by an analog to digital converter during processor 204 activity or during a data transmit occurrence. In a further embodiment, the low pass filter values (i.e., the values of the resistor 405 and the capacitor 406) may be further varied or optimized for a given Power Supply Rejection Ratio (PSRR) of the analog circuitry.

Figure 5A:
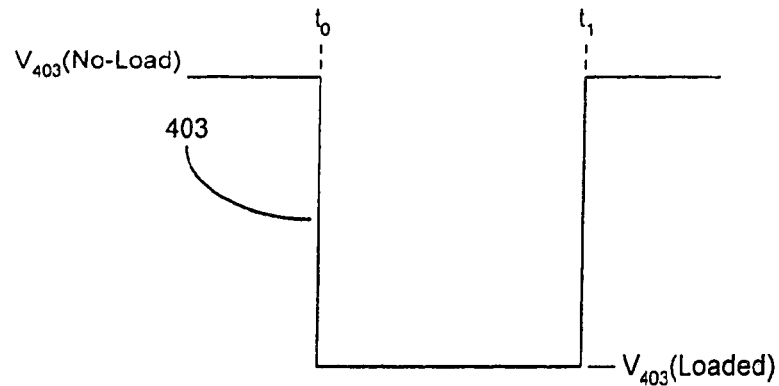
FIGS. 5A-5C illustrate the signal levels at the input to the peak detection circuit, between the output of the peak detection circuit and the input to the low pass filter, and at the output of the low pass filter, respectively, in accordance with one embodiment of the present invention.
Figure 5B:
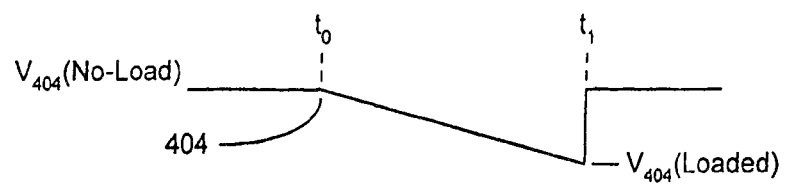
Figure 5C:
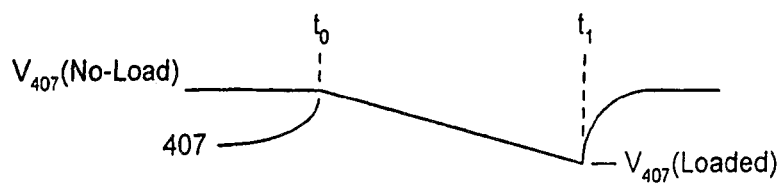

FIGS. 5A-5C illustrate the signal levels at the input to the peak detection circuit, between the output of the peak detection circuit and the input to the low pass filter, and at the output of the low pass filter, respectively, in accordance with one embodiment of the present invention. Referring to FIGS. 4 and 5A-5C, the signal waveform at the input terminal 403 to the peak detection circuit 301 (FIG. 4) is shown in FIG. 5A over the time period $t_0$ to $t_1$, while the signal waveform at the output terminal 404 of the peak detection circuit 301 is shown in FIG. 5B, and the low pass filtered signal at the output terminal 407 of the low pass filter 302 (FIG. 4) is shown in FIG. 5C.

FIGS. 6A-6C illustrate the peak detection circuits implemented using active components in accordance with alternate embodiments of the present invention. More specifically, FIGS. 6A-6C respectively illustrate a relay circuitry 601, a pnp bipolar junction transistor (BJT) switch 602, and a PMOS field effect transistor (FET) switch 603, each configured to operate as active peak detection circuits in accordance with alternate embodiments of the present invention. In the embodiments shown in FIGS. 6A-6C, the peak detection circuits 601-603 are implemented as an inverter so that a low input signal closes the switch, and charges the capacitor, driving the load circuit (e.g., the analog front end circuitry), and a high input signal causes the switch to open and the load circuit in such case is powered by the energy stored in the capacitor.

As each of the switches shown in FIGS. 6A-6C are active switches, they each must be actively switched on and off by the processor 204 each time a voltage drooping is anticipated. By contrast, the passive peak detection circuit using the diode switching system does not require active switching by the processor 204, but rather, is configured to automatically detect such voltage drop due to processor 204 activity or based on the detection of data transmit activities.

By way of example, in the case of using the relay switch 601 or the FET switch 603 as the peak detection circuit 301, the voltage drop between the power supply 207 voltage coupled to the input terminal 403 of the peak detection circuit 301, and the voltage supplied to the analog front end circuitry (for example, at terminal 407 in FIG. 4) may be in the order of 5 mVolts, while the embodiment discussed above using the diode 401 (FIG. 4) may have a 100 mV drop.

In the manner described above, in accordance with the various embodiments of the present invention, there is provided a method and apparatus for isolating potential voltage droop from the power supply 207 to the delicate circuitry of the analog front end in a simple, and cost effective manner while maintaining the level of noise to a minimum.

More specifically, there is provided in one embodiment, a peak detection circuit in the transmitter unit of a data communication system which is configured to detect a voltage droop from its power supply such as a battery configured to power the transmitter, and to effectively compensate for the detected voltage signal droop such that the delicate circuitry of the electrometer and the analog front end circuitry of the transmitter unit may be electrically isolated (for example, by switching off the connection between the electrometer and the analog front end circuitry, and the power supply source) from the detected voltage drooping while the necessary current is drawn from another source such as a capacitor to support the required voltage level of the electrometer and the analog front end circuitry.

The peak detection circuit may include passive switching configurations with a diode and a capacitor combination. In addition, a low pass filter may be operatively coupled to the peak detection circuit to filter out any switching noise transients. In an alternate embodiment, the peak detection circuit may include active components such as a relay switch, a BJT or FET transistor switch. In this case, the switching mechanism is controlled by the processor to turn the switch on or off, in case of power supply voltage drooping, as opposed to the passive component configuration with the diode, in which case such voltage drooping is automatically detected and the switching mechanism of the peak detection circuit accordingly operated in response thereto.

In one embodiment, the diode used for the peak detection circuit may include a Schottky diode switch. Moreover, the peak detection circuit in one embodiment may be provided between the power supply and the analog front end circuitry of the transmitter unit in the continuous glucose monitoring system such that in cases where power supply voltage drooping occurs, the peak detection circuit may be configured to isolate the delicate circuitry of the analog front end of the transmitter unit from the power supply, and rather allow the electrometer and the analog front end circuitry of the transmitter to draw the necessary power from a capacitor of the peak detection circuit to ensure continuous and proper operation.

Accordingly, in accordance with the various embodiments of the present invention, by using a peak detection circuit with a tuned low pass filter, an effective, low cost and low noise approach to isolating the battery droop, even that in excess of 0.5 volts, may be achieved such that in the monitoring system discussed above, the detected and processed data values are not substantially affected, and the delicate analog circuitry of the transmitter is not adversely affected by the fluctuation in power supply signal.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An analyte monitoring assembly, comprising:
   an analyte sensor having a portion configured for transcutaneous positioning in fluid contact with interstitial fluid, the analyte sensor configured to detect an analyte level; and
   a data communication unit including an analog interface operatively coupled to the analyte sensor and configured to receive one or more signals associated with the analyte level, the data communication unit configured to communicate one or more data corresponding to the one or more signals associated with the analyte level, the data communication unit further including a peak detection unit configured to detect a condition associated with a power source of the data communication unit;
      wherein the peak detection unit is configured to electrically isolate the power source of the data communication unit from the analog interface and to provide power to the analog interface when the condition associated with the power source is detected.

2. The assembly of claim 1 wherein the data communication unit is configured to wirelessly communicate the one or more data corresponding to the one or more signals associated with the analyte level to a remote location.

3. The assembly of claim 1 wherein the data communication unit includes a radio frequency antenna for data communication.

4. The assembly of claim 1 wherein the peak detection circuit is configured to provide power to the analog interface of the data communication unit when the analog interface is electrically isolated from the power source of the data communication unit.

5. The assembly of claim 1 wherein the peak detection circuit includes:
   a diode including an input terminal and an output terminal, said input terminal of said diode configured to receive an input signal;
   a capacitor operatively coupled to said output terminal of said diode; and
   an output terminal operatively coupled to said capacitor and said output terminal of said diode for outputting an output signal.

6. The assembly of claim 5 wherein said diode includes a Schottky diode switch.

7. The assembly of claim 5 wherein said input signal includes a voltage signal from the power source.

8. The assembly of claim 5 wherein the detected condition includes a voltage droop associated with the power source.

9. The assembly of claim 8 wherein the voltage droop is detected at said input terminal of said diode, and further, wherein said diode and said capacitor are configured to compensate for said voltage droop.

10. The assembly of claim 1 wherein the detected condition is associated with the communication of the one or more data corresponding to the one or more signals associated with the analyte level.

11. The assembly of claim 1 wherein the analyte sensor includes a glucose sensor.

12. The assembly of claim 1 wherein the analyte sensor includes an electrochemical sensor.

13. The assembly of claim 1 wherein the data communication unit further includes a low pass filter operatively coupled to the peak detection circuit.

14. The assembly of claim 1 wherein said peak detection circuit includes a passive switching configuration.

15. The assembly of claim 1 wherein said peak detection circuit includes a diode operatively coupled to a capacitance.

16. The system of claim 15 wherein said diode includes a Schottky diode switch.

17. A method, comprising:
- transcutaneously positioning an analyte sensor in fluid contact with interstitial fluid;
- detecting an analyte level from the analyte sensor;
- providing one or more signals associated with the detected analyte level from the analyte sensor received by an analog interface of a data communication device;
- detecting a predetermined condition associated with a power source; and
- electrically isolating the analog interface from the power source when the predetermined condition is detected; and
- supplying power to the analog interface from a source other than the power source when the predetermined condition is detected;
    - wherein the one or more signals associated with the detected analyte level from the analyte sensor are communicated during the time period when the predetermined condition is detected.

18. The method of claim 17 wherein the one or more signals associated with the detected analyte level is wirelessly communicated to a remote location.

19. The method of claim 17 including coupling the analog interface to the power source when the predetermined condition is no longer detected.

20. The method of claim 17 wherein the source other than the power source for supplying power to the analog interface when the predetermined condition is detected includes a peak detection circuit.

* * * * *